US008754049B2

(12) United States Patent
Fischer et al.

(10) Patent No.: US 8,754,049 B2
(45) Date of Patent: Jun. 17, 2014

(54) ORGANIC COMPOUND FOR THE REGULATION OF VECTORIAL ION CHANNELS

(75) Inventors: Bernhard Fischer, Vienna (AT); Rudolf Lucas, Antwerp (BE); Susan Tzotzos, Vienna (AT)

(73) Assignee: APEPTICO Forschung und Entwicklung GmbH, Vienna (AT)

( * ) Notice: Subject to any disclaimer, the term of this patent is extended or adjusted under 35 U.S.C. 154(b) by 0 days.

(21) Appl. No.: 13/522,204

(22) PCT Filed: Jan. 12, 2011

(86) PCT No.: PCT/AT2011/000014
§ 371 (c)(1),
(2), (4) Date: Jul. 13, 2012

(87) PCT Pub. No.: WO2011/085423
PCT Pub. Date: Jul. 21, 2011

(65) Prior Publication Data
US 2013/0072444 A1    Mar. 21, 2013

(30) Foreign Application Priority Data

Jan. 14, 2010    (AT) .................................. A 41/2010

(51) Int. Cl.
*A61K 38/12* (2006.01)
*A61K 38/00* (2006.01)
*A61K 38/16* (2006.01)
*A61K 38/10* (2006.01)
*A61K 38/04* (2006.01)
*A61P 11/00* (2006.01)
*C07K 5/00* (2006.01)
*C07K 7/00* (2006.01)
*C07K 16/00* (2006.01)
*C07K 17/00* (2006.01)

(52) U.S. Cl.
USPC ......... 514/21.1; 514/1.5; 514/17.4; 514/21.4; 530/317; 530/323; 530/326; 530/332

(58) Field of Classification Search
None
See application file for complete search history.

(56) References Cited

U.S. PATENT DOCUMENTS

| 7,258,861 B2 * | 8/2007 | Lucas et al. ................ 424/185.1 |
| 2003/0185791 A1 | 10/2003 | Lucas et al. |
| 2006/0241026 A1 * | 10/2006 | Romestand et al. .............. 514/9 |
| 2011/0021411 A1 * | 1/2011 | Fischer et al. ................. 514/1.1 |
| 2011/0105414 A1 * | 5/2011 | Fischer et al. ............... 514/21.1 |
| 2011/0319316 A1 * | 12/2011 | Fischer et al. ................. 514/1.5 |
| 2013/0116200 A1 * | 5/2013 | Fischer et al. ............... 514/21.1 |

FOREIGN PATENT DOCUMENTS

| EP | 2 009 023 | 12/2008 | |
| WO | WO00/09149 | 2/2000 | |
| WO | WO 0009149 A1 * | 2/2000 | ............. A61K 38/19 |
| WO | WO2006/013183 | 2/2006 | |
| WO | WO 2008148545 A1 * | 12/2008 | .......... C07K 14/525 |
| WO | WO2009/073909 | 6/2009 | |
| WO | WO2010/099556 | 9/2010 | |

OTHER PUBLICATIONS

U.S. Appl. No. 13/805,839, filed Dec. 2012, Fischer et al.*
Hazemi et al., "Essential Structural Features of TNF-alpha Lectin-like Domain Derived Peptides for activation of Amiloride-Sensitive Sodium Current in A549 Cells," J. Med. Chem. 53:8021-8029 (2010).*
Kopple, K.D., "Synthesis of Cyclic Peptides," J. Pharm. Sci. 61:1345-1356 (1972).*
Berthiaume Y. and Matthay M.A.; *Respiratory Physiology & Neurobiology*; Alveolar Edema Fluid Clearance and Acute Lung Injury; vol. 159 (2007); pp. 350-359.
Clunes M.T. et al.; *J Physiolo*.; (2004) vol. 557.3; pp. 809-819.
Hamill et al; *Pflugers Arch.*; vol. 391, No. 2; pp. 85-100; (1981).
Hazemi, et al.; *Journal of Medicinal Chemistry*; "Essential Structural Features of TNF-alpha Lectin-like Domain Derived Peptides for Activation of Amiloride-sensitive Sodium Current in A549 Cells;" Bd. 53, No. 22; Oct. 27, 2010, pp. 8021-8029.
Lucas, et al ; *Science*; "Mapping the Lectin-Like Activity of Tumor Necrosis Factor;" 1994, vol. 263:; p. 814.
Matthay et al.; *Am J Physiol.*; "Salt and Water Transport Across Alveolar and Distral Airway Epithelia in the Adult Lung;" 1996; vol. 270; pp. L487-L503.
Ware L.B. and Matthay M.A.; *New England J Med.*; "The Acute Respiratory Distress Syndrome;" 2001; vol. 342, No. 18; pp. 1334-1359.

* cited by examiner

Primary Examiner — Marcela M Cordero Garcia
Assistant Examiner — Thea D'Ambrosio
(74) Attorney, Agent, or Firm — D. Peter Hochberg; Sean F. Mellino; Richard A. Wolf

(57) ABSTRACT

A cyclic organic compound which comprises 16 amino acids or 17 amino acids and has no carboxyl group C-terminally and/or no amino group N-terminally. Optionally, one of the amino acids is a nonnatural amino acid. The ring closure is formed between a side chain of one amino acid and the C-terminus of another amino acid, or the ring closure is effected with the aid of a nonnatural amino acid. A process for producing and using the compound for regulating vectorial ion channels, for treating diseases associated with the lung function and for treating oedemas is provided.

9 Claims, 16 Drawing Sheets

ORGANIC COMPOUND FOR THE REGULATION OF VECTORIAL ION CHANNELS

CROSS-REFERENCE TO RELATED APPLICATIONS

This application is a National Stage application of International Application No. PCT/AT2011/000014, filed on Jan. 12, 2011, which claims priority of Austrian application Serial Number A 41/2010, filed on Jan. 14, 2010, both of which are incorporated herein by reference in their entireties.

BACKGROUND OF THE INVENTION

1. Field of the Invention

The invention relates to organic compounds and pharmaceutical preparations thereof which are suitable for the regulation of vectorial ion channels, of diseases associated with the lung function and for the treatment of oedemas.

2. Description of the Prior Art

The fluid transport through cell layers and tissue is primarily based on an osmotic gradient by a vectorial ion transport, e.g., sodium transport. It is accomplished mainly by strictly regulated and vitally important ion channels such as, e.g., the epithelial sodium channel complex (ENaC) (Ware L. B. and Matthay M. A. New England J Med 2001; 342/18: 1334-1359. Matthay et al., Am J Physiol 1996; 270:L487-L503; Berthiaume Y. and Matthay M. A. Respiratory Physiology & Neurobiology 159 (2007) 350-359). Water passively follows this gradient, inter alia, through special water channels such as the water channel Aquaporin V. Therefore, a medicinal regulation of the vectorial ion transport through cells and tissue would result in the possibility of controlling the fluid content of tissues as well as of preventively or therapeutically treating diseases which are associated with an accumulation of fluid in the tissue.

If an oedema is mentioned, a pathological accumulation of fluid in an organ such as, e.g., in the lungs, but also in the brain or in the skin, is meant. An oedema in the lungs is called a pulmonary oedema. The pulmonary oedema is mostly based on an imbalance between fluid extravasation and fluid resorption. Very often, the permeability of the lung tissue is also damaged so that an increased fluid supply occurs and the fluid accumulates in the pulmonary alveoli.

A pulmonary oedema as a result of a lack of return transport of fluid from the pulmonary alveoli into the interstice is particularly significant for an Acute Lung Injury, ALI, for the Acute Respiratory Distress Syndrome, ARDS, for the Severe Acute Respiratory Syndrome (SARS), for pneumonia, for influenza and for other bacterially and virally induced lung diseases. However, the pulmonary oedema also plays a significant part in other lung diseases such as respiration-induced lung injuries, lung transplants, transfusion-associated lung injuries, therapeutical administration of IL-2 or asthma.

As a result of an increased fluid accumulation in the tissue or organ, e.g., in the lungs, the required gas exchange is impeded or completely restricted. No oxygen from the breathing air reaches the blood so that life-threatening organ damages may occur due to oxygen deficiency.

Lucas et al (Lucas R et al. Science 1994, 263: 814) describe a peptide which is derived from the regions Ser(99) to Glu (116) of the tumour necrosis factor and is supposed to control the fluid content in the pulmonary alveoli.

Said peptide comprising the sequences SEQ ID NO: 10 CGQRETPEGAEKPWYC is also the subject matter of WO00/09149.

A peptide also for controlling the fluid content in the alveoli and comprising the sequence SEQ ID NO: 11 CGT-KPIELGPDEPKAVC is included in EP 2 009 023, and a peptide comprising the sequence SEQ ID NO: 12 LSPGQRETPEGAEAKPWYE is included in WO2009/073909.

So far, there has been no selective and medically usable therapy or treatment for the regulation of vectorial ion channels in cells and tissues, in particular for the regulation of vectorial ion channels of the lung tissue. Neither has there been so far a selective therapy for the regulation of the vectorial ion transport in the lungs and in particular for the treatment of pulmonary oedemas. Quite generally, it is attempted to give artificial respiration to patients suffering from pulmonary oedemas in order to ensure the supply of oxygen to the blood and thus to the organs.

SUMMARY OF THE PRESENT INVENTION

Thus, the present invention is based on the object of providing organic and bio-active substances which are suitable for the vectorial activation of ion channels. In particular, the present invention is aimed at providing organic and bio-active substances which can be used for the activation of epithelial sodium ion channels in the lungs and for a selective treatment of the pulmonary oedema.

Surprisingly, organic compounds have now been found which are suitable for solving the problem that has been set.

In one aspect, the present invention provides a cyclic organic compound which is characterized in that it comprises 16 amino acids or 17 amino acids and has no carboxyl group C-terminally and/or no amino group N-terminally, wherein, optionally, one of the amino acids is a nonnatural amino acid, and wherein the ring closure is formed between a side chain of one amino acid and the C-terminus of another amino acid, or the ring closure is effected with the aid of a nonnatural amino acid.

A cyclic organic compound or cyclic organic compounds which is/are provided according to the present invention is/are referred to in this application also as "compound(s) according to the present invention".

A compound according to the present invention includes a compound in any form, e.g., in free form and in the form of co-crystals, e.g., in the form of a salt, or in the form of a solvate, or in the form of a salt and a solvate.

In a further aspect, the present invention provides a compound according to the present invention in the form of a salt. Preferably, such salts include pharmaceutically acceptable salts, although pharmaceutically unacceptable salts are included, for example, for the purpose of manufacturing, isolating, purifying a compound of the present invention. For example, the present invention includes a salt of a compound of the present invention with trifluoroacetic acid, which may occur, for example, during the manufacture of a compound of the present invention.

A compound according to the present invention in the form of a salt includes a metal salt or an acid addition salt. Metal salts include, e.g., alkali or alkaline earth salts, acid addition salts include a salt of a compound according to the present invention with an acid.

A compound according to the present invention in free form, optionally in the form of a solvate, can be converted into an appropriate compound in the form of a salt, in a nonsolvate form or in the form of a solvate, and vice versa.

In compounds according to the present invention, certain amino acid sequences in combination with ring closures which, so far, have been unknown for peptides surprisingly result in cyclic organic compounds, while forming an intramolecular amide bond which, so far, has not been known for peptides, wherein such compounds are able, completely unexpectedly, to regulate vectorial ion channels in cells and tissues, for example, compounds of the present invention are able to regulate the epithelial sodium channel complex, partly to a larger extent than previously known, but structurally different peptides.

Surprisingly, it has turned out that a compound according to the present invention comprises the amino acid sequence SEQ ID NO: 9 GQRETPEGAEAKPWY.

In another aspect, the present invention provides a compound according to the present invention which comprises the amino acid sequence SEQ ID NO: 9 GQRETPEGAEAK-PWY.

The nonnatural amino acid in a compound according to the present invention is preferably selected from ornithine or an omega-amino acid, in particular an omega-amino-$(C_{3-8})$-alkanoic acid, in particular from 3-amino-propanoic acid, gamma-aminobutyric acid, 5-amino-pentanoic acid, 6-amino-hexanoic acid and 7-amino-heptanoic acid, in particular, the nonnatural amino acid is linked via amide bonds.

In a further aspect, the present invention provides a compound according to the present invention in which the nonnatural amino acid is selected from ornithine or an omega-amino acid; in particular, the nonnatural amino acid is linked via amide bonds.

In a compound according to the present invention, the ring closure is preferably formed between a side chain of one amino acid and the C-terminus of another amino acid, in particular, between a side chain of the ornithine or lysine and the C-terminus of a natural amino acid, in particular of a glycine.

In a further aspect, the present invention provides a compound according to the present invention which is characterized in that the ring closure is formed between a side chain of one amino acid and the C-terminus of another amino acid.

In a further aspect, the present invention provides a compound according to the present invention comprising the amino acid sequences

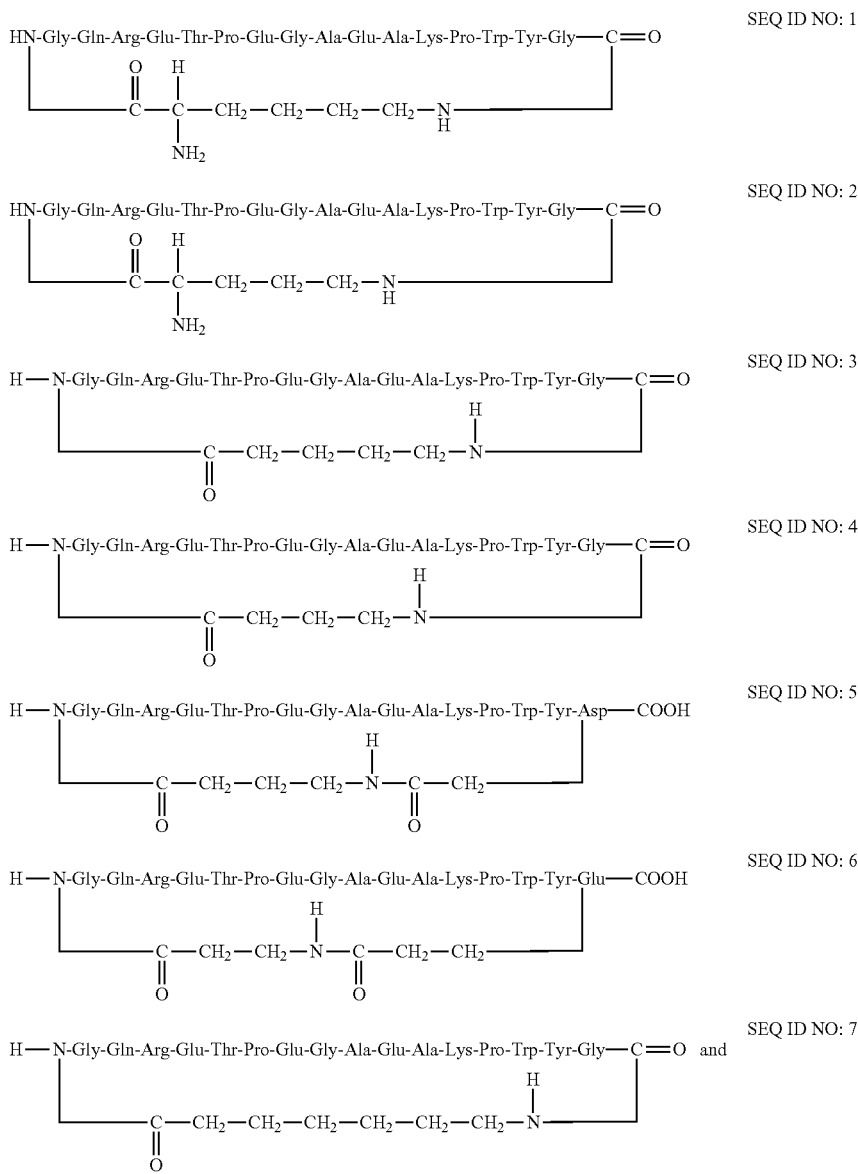

-continued

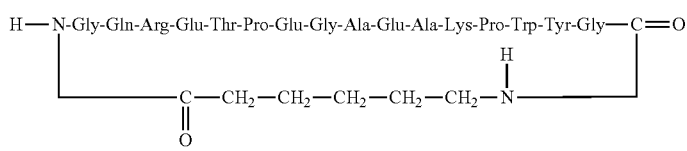

SEQ ID NO: 8

In a compound of sequence SEQ ID NO: 1 {[KGQRET-PEGAEAKPWYG] (cyclo Kepsilon1-G17)}, the amino acids are peptidically linked from the C-terminal amino acid glycine (G) to the N-terminal amino acid lysine (K), whereas the N-terminal amino acid lysine (K) is linked to the C-terminal amino acid glycine (G) via an amide bond between the nitrogen of the epsilon-amino group of the side chain of the lysine and the carbon of the carboxyl group of the glycine so that the compound has no C-terminal carboxyl group.

In a compound comprising the sequence SEQ ID NO: 2 {[ornithine-GQRETPEGAEAKPWYG] (cyclo Orn-delta1-G17)}, the amino acids are peptidically linked from the C-terminal amino acid glycine (G) to the N-terminal amino acid ornithine (Orn), whereas the N-terminal amino acid ornithine (Orn) is linked to the C-terminal amino acid glycine (G) via an amide bond between the nitrogen of the delta-amino group of the side chain of the ornithine and the carbon of the carboxyl group of the glycine so that the compound has no C-terminal carboxyl group.

In a compound comprising the sequence SEQ ID NO: 3 {[5-amino-pentanoic acid-GQRETPEGAEAKPWYG] (cyclo 1-17)}, the amino acids are peptidically linked from the C-terminal amino acid glycine (G) to the N-terminal amino acid glycine (G), whereas the N-terminal amino acid glycine (G) is linked to the C-terminal amino acid glycine (G) via an amide bond between the nitrogen of the amino group of the N-terminal glycine and the carbon C1 of the carboxyl group of the 5-amino-pentanoic acid, on the one hand, and by an amide bond between the nitrogen of the 5-amino group of the 5-amino-pentanoic acid and the carbon of the carboxyl group of the C-terminal glycine, on the other hand, so that the compound has no C-terminal carboxyl group.

In a compound comprising the sequence SEQ ID NO: 4 {[gamma-aminobutyric acid-GQRETPEGAEAKPWYG] (cyclo 1-17)}, the amino acids are peptidically linked from the C-terminal amino acid glycine (G) to the N-terminal amino acid glycine (G), whereas the C-terminal amino acid glycine (G) is linked to the N-terminal amino acid glycine (G) via an amide bond between the nitrogen of the amino group of the N-terminal glycine and the carbon C1 of the carboxyl group of the gamma-aminobutyric acid, on the one hand, and via an amide bond between the nitrogen of the amino group of the gamma-aminobutyric acid and the carbon of the carboxyl group of the C-terminal glycine, on the other hand, so that the compound has no C-terminal carboxyl group.

In a compound comprising the sequence SEQ ID NO: 5 {[gamma-aminobutyric acid-GQRETPEGAEAKPWYD-OH] (cyclo 1-Dγ17)}, the amino acids are peptidically linked from the C-terminal aspartic acid (D) to the N-terminal amino acid glycine, whereas the C-terminal aspartic acid (D) is linked to the N-terminal amino acid glycine via an amide bond between the nitrogen of the amino group of the N-terminal glycine and the carbon C1 of the carboxyl group of the gamma-aminobutyric acid, on the one hand, and via an amide bond between the nitrogen of the amino group of the gamma-aminobutyric acid and the carbon of the carboxyl group of the side chain of the C-terminal aspartic acid, on the other hand, so that the compound has no N-terminal amino group.

In a compound comprising the sequence SEQ ID NO: 6 {[3-amino-propanoic acid-GQRETPEGAEAKPWYE-OH] (cyclo 1-Eδ17)}, the amino acids are peptidically linked from the C-terminal glutamic acid (E) to the N-terminal amino acid glycine, whereas the C-terminal glutamic acid (E) is linked to the N-terminal amino acid glycine via an amide bond between the nitrogen of the amino group of the N-terminal glycine and the carbon C1 of the carboxyl group of the 3-amino-propanoic acid, on the one hand, and via an amide bond between the nitrogen of the amino group of the 3-amino-propanoic acid and the carbon of the carboxyl group of the side chain of the C-terminal glutamic acid, on the other hand, so that the compound has no N-terminal amino group.

In a compound comprising the sequence SEQ ID NO: 7 {[7-amino-heptanoic acid-GQRETPEGAEAKPWY] (cyclo 1-16)}, the amino acids are peptidically linked from the C-terminal amino acid tyrosine to the N-terminal amino acid glycine, whereas the C-terminal amino acid tyrosine is linked to the N-terminal amino acid glycine via an amide bond between the nitrogen of the amino group of the N-terminal glycine and the carbon C1 of the carboxyl group of the 7-amino-heptanoic acid, on the one hand, and via an amide bond between the nitrogen of the amino group of the 7-amino-heptanoic acid and the carbon of the carboxyl group of the C-terminal tyrosine, on the other hand, so that the compound has neither an N-terminal amino group, nor a C-terminal carboxyl group.

In a compound comprising the sequence SEQ ID NO: 8 {[6-amino-hexanoic acid-GQRETPEGAEAKPWYG] (cyclo 1-17)}, the amino acids are peptidically linked from the C-terminal amino acid glycine to the N-terminal amino acid glycine, whereas the C-terminal amino acid glycine is linked to the N-terminal amino acid glycine via an amide bond between the nitrogen of the amino group of the N-terminal glycine and the carbon C1 of the carboxyl group of the 6-amino-hexanoic acid, on the one hand, and via an amide bond between the nitrogen of the amino group of the 6-amino-hexanoic acid and the carbon of the carboxyl group of the C-terminal glycine, on the other hand, so that the compound has neither an N-terminal amino group, nor a C-terminal carboxyl group.

A compound according to the present invention can be produced in a suitable manner, e.g., analogously to a known process, or as described herein, for example, by chemical synthesis or using microbial processes, wherein, in particular, the introduction of an amide bond between a free amino group and a free carboxyl group may occur in a suitable manner, e.g., analogously to a known process, or as described in the present application.

It has turned out that a compound according to the present invention shows an interesting pharmacological activity and thus can be used as a medicament.

In a further aspect, the present invention provides a compound according to the present invention for use as a medicament.

Biological examinations on human cells show that the compounds according to the present invention exhibit no inflammatory or toxic properties. To this end, human epithelial cells are cultivated in a common laboratory cell culture, and a compound according to the present invention is added. Despite the addition of a compound according to the present invention, no toxic or inflammatory reactions were observed in the human cells.

The detection of a vectorial regulation of ion channels by a compound may be effected according to a method common in laboratories, for example, according to Clunes M. T. et al., J. Physiolo. (2004) 557.3: 809-819), via patch-clamp experiments. For patch-clamp examinations of ion channels, a glass cannula is stretched thin and filled with a neutral buffer solution. The glass cannula (patch-clamp pipette) is carefully pressed onto an intact epithelial cell. A piece of membrane is located below the pipette. An electrical resistance is thereby produced between the interior of the pipette and the external solution. An electrode attached to a sensitive amplifier dips into the pipette solution.

A regulation of the vectorial epithelial ion channels is detected via a change in the current intensity with a constant voltage.

In this way, it has surprisingly turned out that the compounds of the present invention exhibit a regulation of the vectorial epithelial ion channels.

It has been particularly surprising that compounds according to the present invention, e.g., compounds comprising the amino acid sequences SEQ ID NO: 1, SEQ ID NO: 2, SEQ ID NO: 5, SEQ ID NO: 6 and SEQ ID NO: 8, result in significantly higher activations of the vectorial ionic current than do the peptides SEQ ID NO: 10 CGQRETPEGAEKPWYC (Lucas et al. Science 1994, also WO00/09149), SEQ ID NO: 11 CGTKPIELGPDEPKAVC (SEQ ID No. 2 from EP 2009 023) and SEQ ID NO: 12 LSPGQRETPEGAEAKPWYE (SEQ ID No. 2 from PCT AT2008 448=WO 2009/073909), which are already known from the literature.

A compound according to the present invention can thus be used for the production of a medicament, e.g., for the regulation of vectorial ion channels, in particular of ion channels in the lungs, and for the treatment of oedemas, in particular for treating the pulmonary oedema; and, in a further aspect, the present invention provides a compound according to the present invention for the production of a medicament for the regulation of vectorial ion channels, in particular of ion channels in the lungs, for the treatment of diseases associated with the lung function and for the treatment of oedemas, in particular for treating the pulmonary oedema.

The treatment of diseases associated with the lung function includes, for example, the activation of epithelial ion channels, the improvement of the lung function and/or the treatment of oedemas such as pulmonary oedemas, furthermore, the treatment

- of Acute Lung Injury, ALI,
- of Acute Respiratory Distress Syndrome, ARDS,
- of Severe Acute Respiratory Syndrome (SARS),
- of pneumonia,
- of viral pneumonias such as influenza and RSV infections,
- in case of multi-organ failure,
- in case of respiration-induced lung injuries, lung transplants, transfusion-associated lung injuries, therapeutical administration of IL-2 or asthma.

In another aspect, the present invention provides a process for the regulation of vectorial ion channels, in particular of ion channels in the lungs, for the treatment of diseases associated with the lung function, and for the treatment of oedemas, in particular for treating the pulmonary oedema, which is characterized in that an effective amount of a compound according to the present invention is administered to a patient in need of such a treatment.

A patient, as used herein, includes mammals, e.g., humans.

A compound according to the present invention can be administered in the form of a pharmaceutical preparation.

In another aspect, the present invention provides a pharmaceutical preparation which is characterized in that it comprises a compound according to the present invention, e.g., in combination with at least one pharmaceutically acceptable adjuvant such as carriers or diluents, for example, in combination with one or several fillers, binders, disintegrants, flow-conditioning agents, lubricants, flavouring agents, sugar or sweeteners, fragrances, preservatives, substances having a stabilizing effect, wetting agents, emulsifiers, solubilizers, salts for regulating the osmotic pressure and/or buffer (mixtures).

The suitable amount of a compound according to the present invention for the treatment of diseases will of course depend strongly on different parameters, for example, the chemical nature and the pharmacokinetics of the compound used, the individual patient, the disease to be treated, the type of application; however, a successful daily dose for larger mammals includes, for example, an amount ranging from 0.0001 g to 1.5 g, e.g., from 0.001 mg/kg body weight to about 20 mg/kg body weight.

Compounds according to the present invention can be administered in free form or in the form of a salt, optionally in the form of a solvate. A compound according to the present invention in the form of a salt, optionally in the form of a solvate, exhibits essentially the same activity as does a compound of the present invention in free, optionally non-solvated, form.

The administration of a compound according to the present invention or of a pharmaceutical preparation thereof may preferably occur pulmonarily or parenterally and occurs particularly preferably pulmonarily.

A pharmaceutical preparation according to the present invention can be produced in a suitable manner, e.g., analogously to a known method, e.g., by mixing, granulation, coating, dissolution, lyophilization methods.

In the chromatograms of FIG. 1 to FIG. 8, the absorption [mAU=Milli Absorption Unit] is plotted on the y-axis, and the time [minutes] is plotted on the x-axis.

Figure 1:
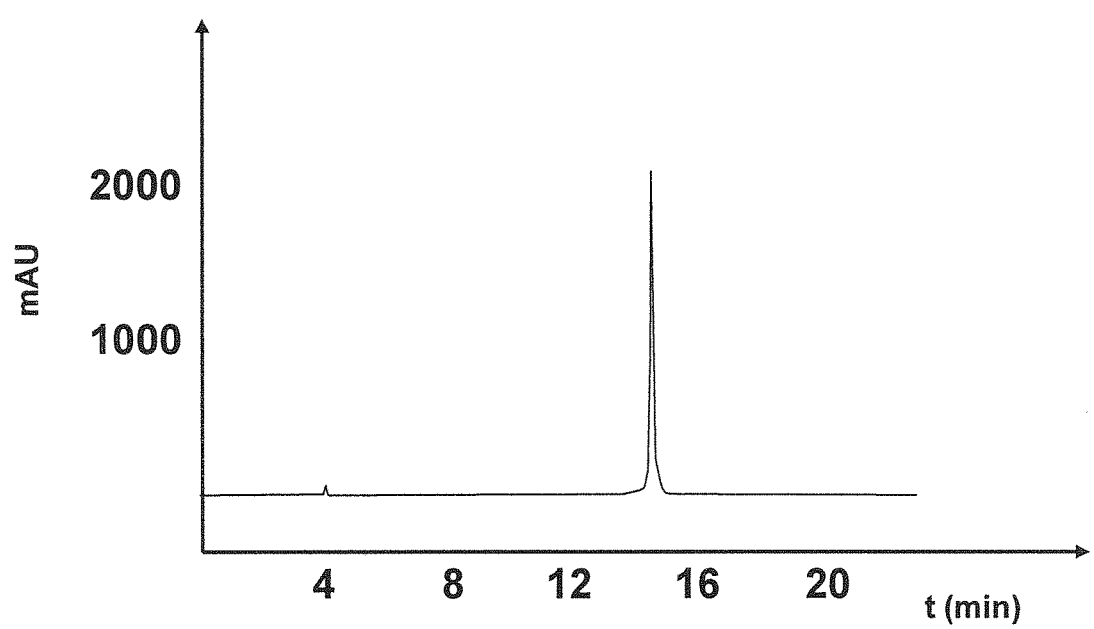
FIG. 1 shows the HPLC chromatogram of a compound comprising amino acid sequence SEQ ID NO: 1.
Figure 2:
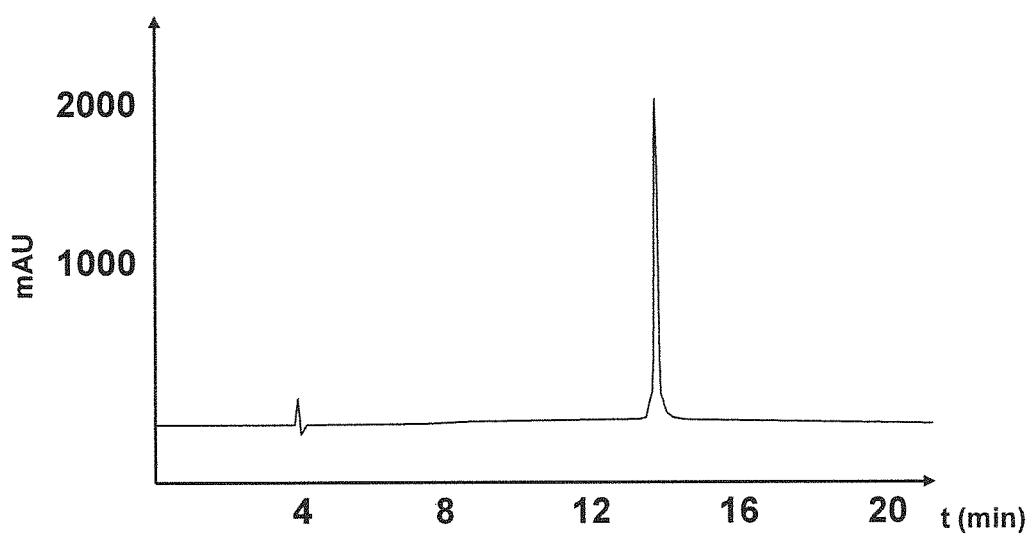
FIG. 2 shows the HPLC chromatogram of a compound comprising amino acid sequence SEQ ID NO: 2.
Figure 3:
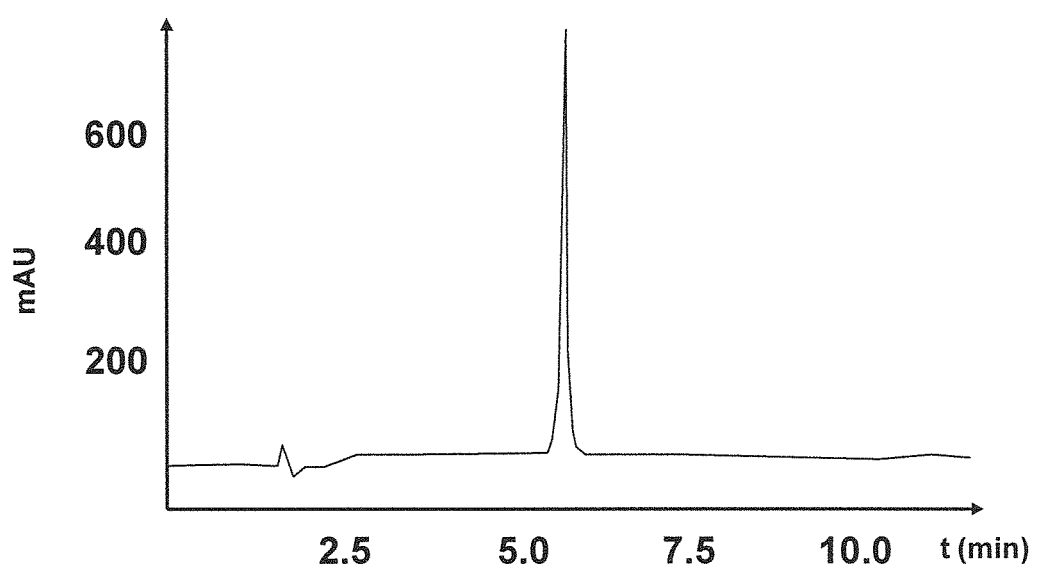
FIG. 3 shows the HPLC chromatogram of a compound comprising amino acid sequence SEQ ID NO: 3.
Figure 4:
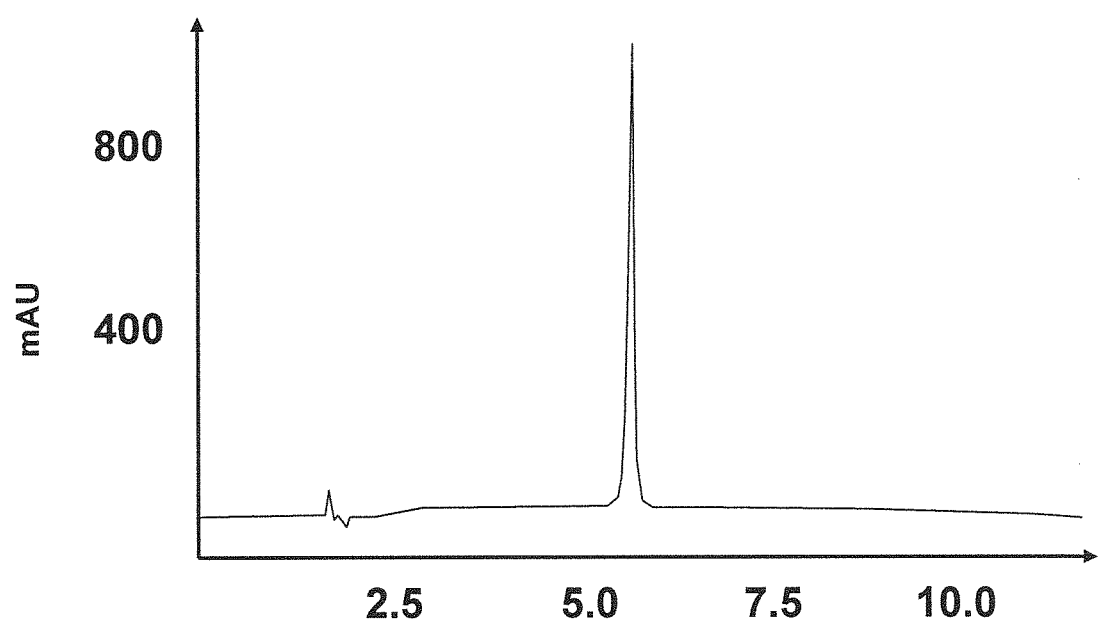
FIG. 4 shows the HPLC chromatogram of a compound comprising amino acid sequence SEQ ID NO: 4.
Figure 5:
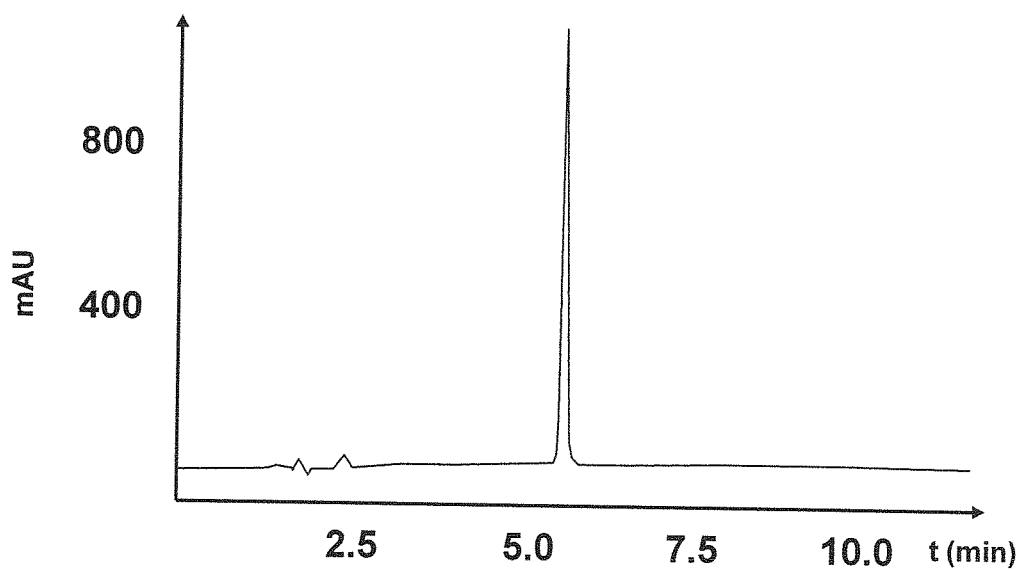
FIG. 5 shows the HPLC chromatogram of a compound comprising amino acid sequence SEQ ID NO: 5.
Figure 6:
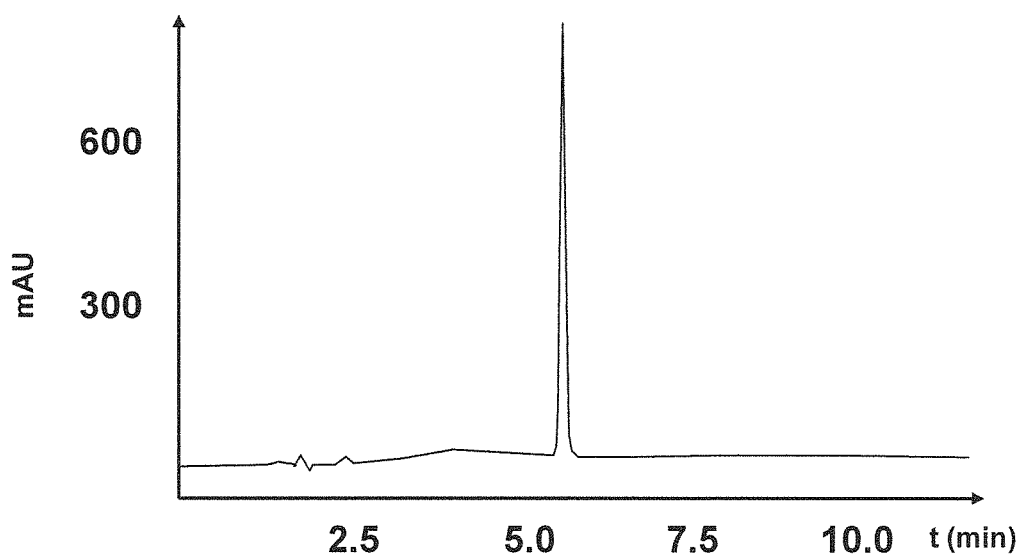
FIG. 6 shows the HPLC chromatogram of a compound comprising amino acid sequence SEQ ID NO: 6.
Figure 7:
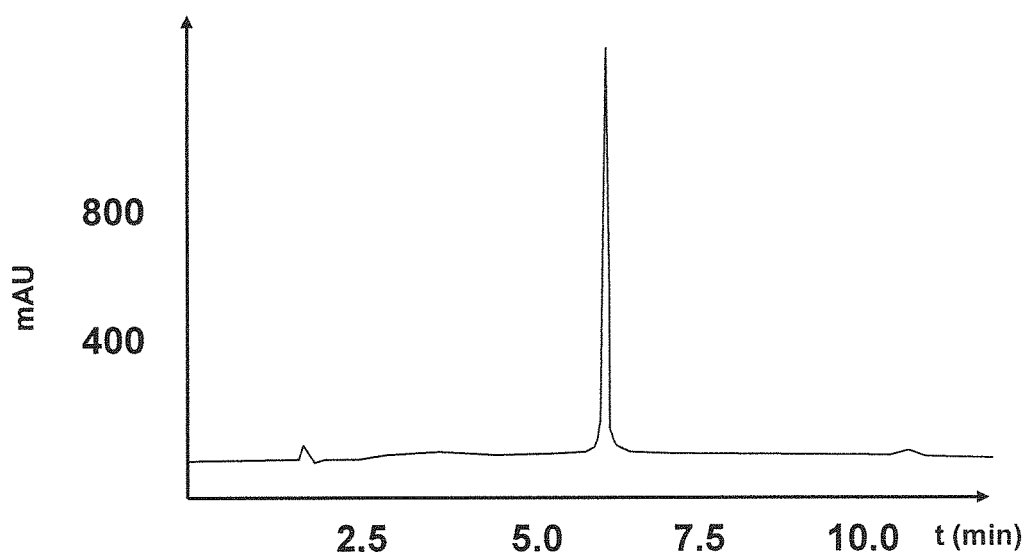
FIG. 7 shows the HPLC chromatogram of a compound comprising amino acid sequence SEQ ID NO: 7.
Figure 8:
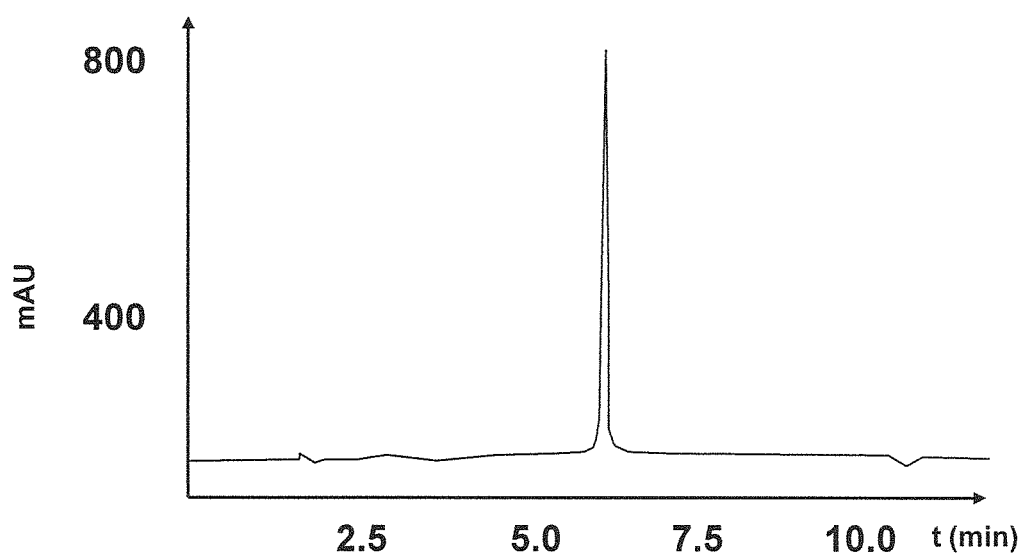
FIG. 8 shows the HPLC chromatogram of a compound comprising amino acid sequence SEQ ID NO: 8.
Figure 9:
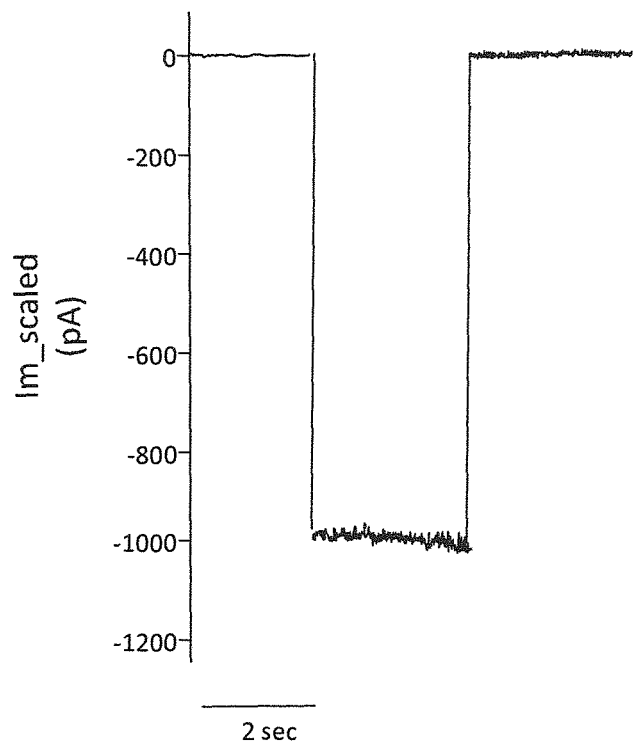

FIG. 9 shows the chromatogram of the patch-clamp measurement of a compound comprising amino acid sequence SEQ ID NO: 1.

Figure 10:
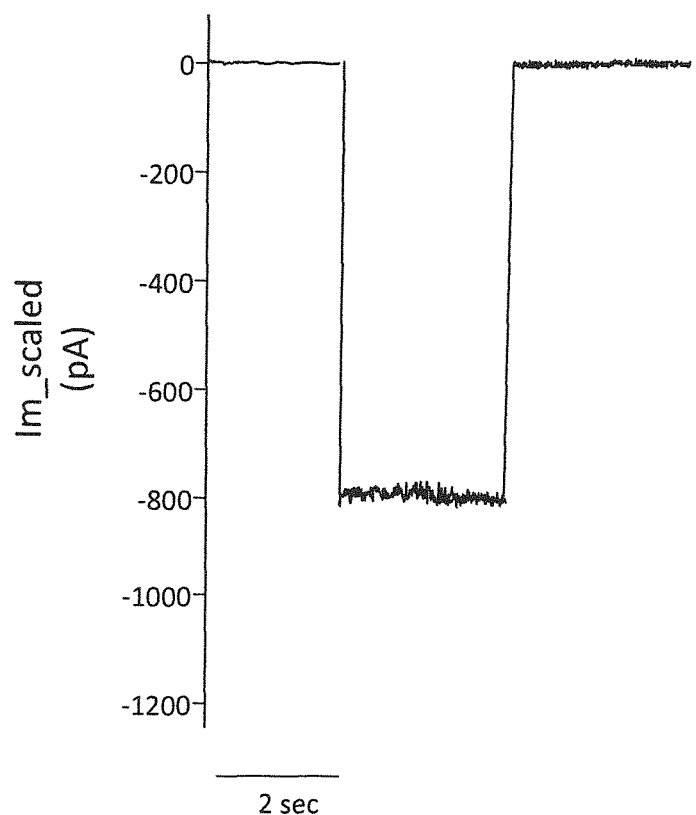

FIG. 10 shows the chromatogram of the patch-clamp measurement of a compound comprising amino acid sequence SEQ ID NO: 2.

Figure 11:
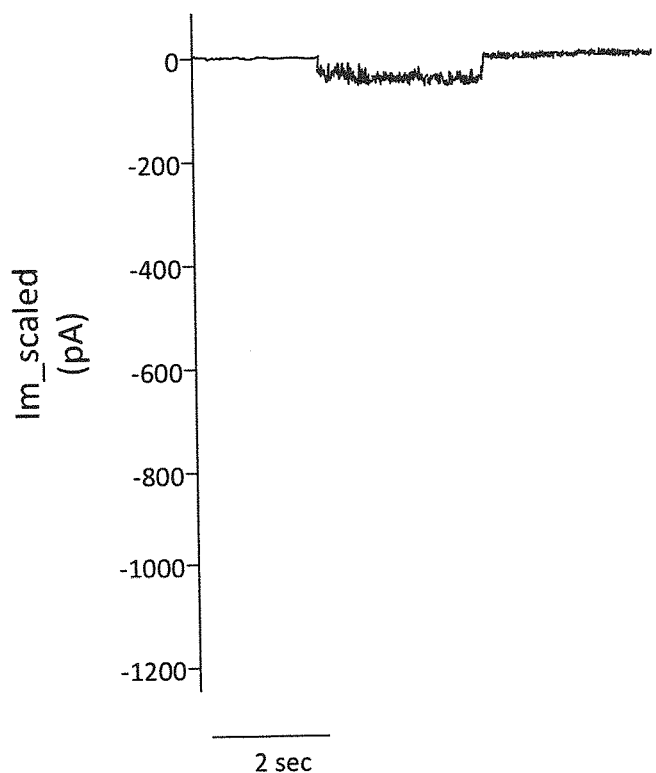

FIG. 11 shows the chromatogram of the patch-clamp measurement of a compound comprising amino acid sequence SEQ ID NO: 3.

Figure 12:
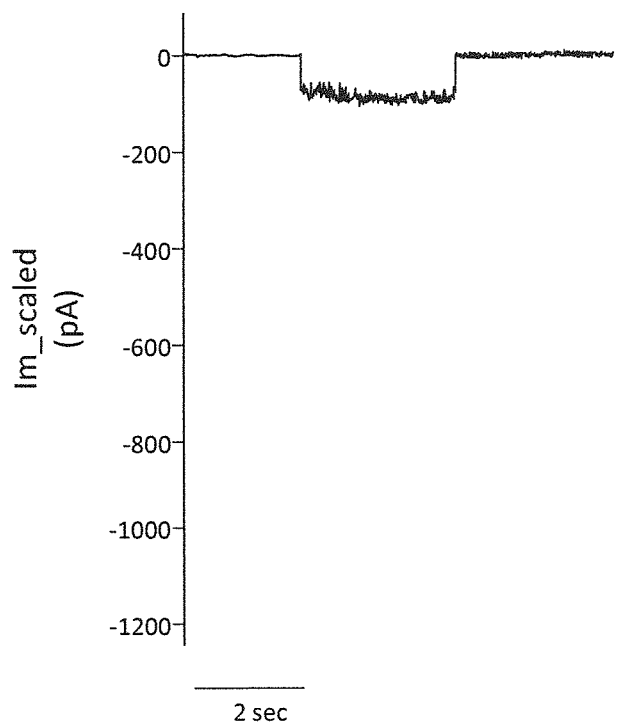

FIG. 12 shows the chromatogram of the patch-clamp measurement of a compound comprising amino acid sequence SEQ ID NO: 4.

Figure 13:
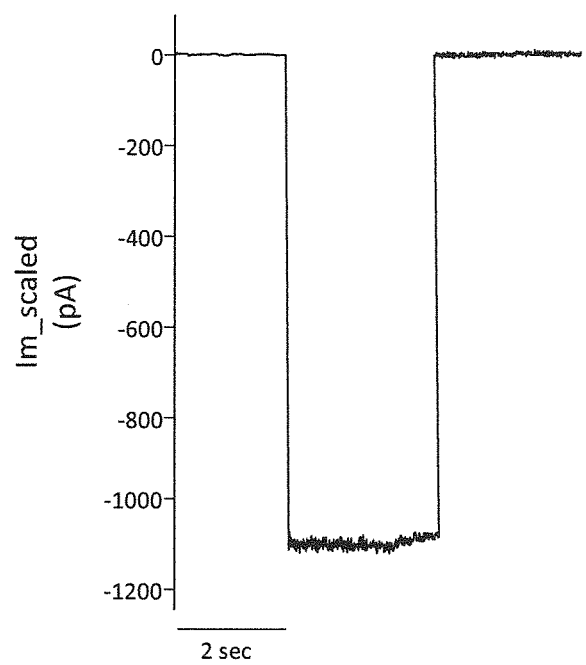

FIG. 13 shows the chromatogram of the patch-clamp measurement of a compound comprising amino acid sequence SEQ ID NO: 5.

Figure 14:
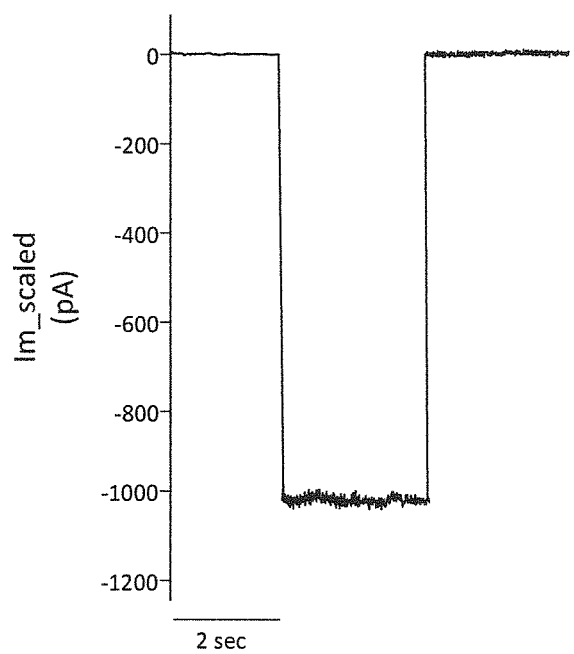

FIG. 14 shows the chromatogram of the patch-clamp measurement of a compound comprising amino acid sequence SEQ ID NO: 6.

Figure 15:
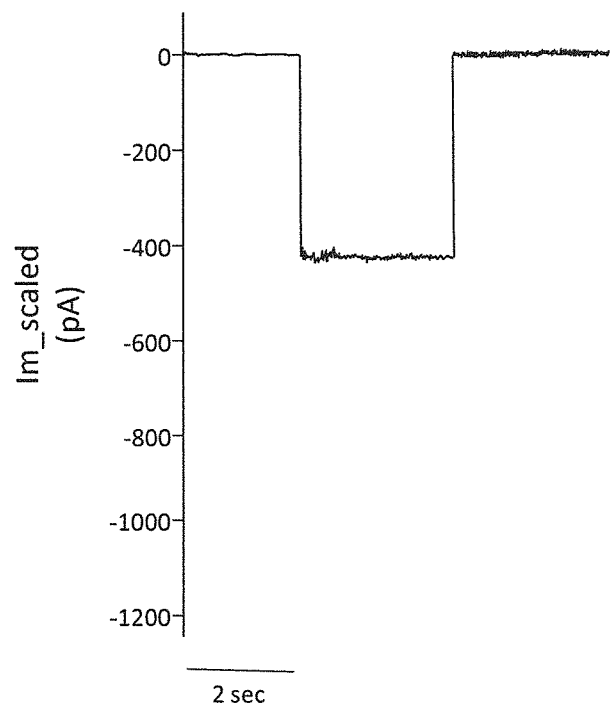

FIG. 15 shows the chromatogram of the patch-clamp measurement of a compound comprising amino acid sequence SEQ ID NO: 7.

Figure 16:
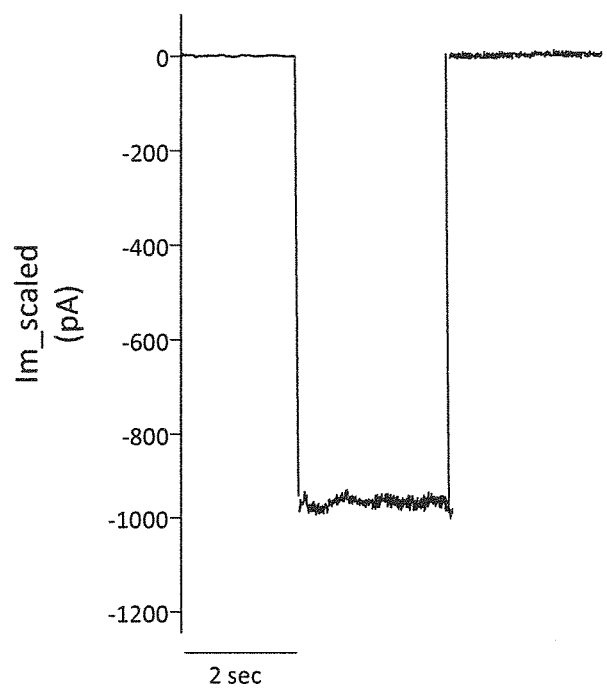

FIG. 16 shows the chromatogram of the patch-clamp measurement of a compound comprising amino acid sequence SEQ ID NO: 8.

In the chromatograms of FIG. 9 to FIG. 16, the current intensity [pA=Picoampere] is plotted on the y-axis, and the time [sec=seconds] is plotted on the x-axis.

DETAILED DESCRIPTION OF THE PRESENT INVENTION

Example 1

Synthesis of a Compound Comprising Amino Acid Sequence SEQ ID NO: 1

The compound comprising the amino acid sequence SEQ ID NO: 1 was synthesized fully automatically via Fmoc solid-phase synthesis in steps which are described in table 1:

TABLE 1

| Step | Process | Product |
|---|---|---|
| 1 | sequential coupling of amino acids | growing peptide chain, bound to the solid phase |
| 2 | selective splitting from the solid phase | partly protected peptide in solution |
| 3 | purification and lyophilization | purified, partly protected peptide |
| 4 | selective cyclization | partly protected, cyclized peptide |
| 5 | cleavage of protective groups | cyclized peptide in solution |
| 6 | purification and lyophilization | purified, cyclized peptide as a trifluoroacetic acid salt |
| 7 | analytical examination | purified peptide |

The ring closure was effected by the formation of an amide bond between the nitrogen of the epsilon-amino group of the side chain of the N-terminal lysine and the carbon of the carboxyl group of the C-terminal glycine.

Subsequently, the peptide was examined via reverse HPLC. The purity was more than 95%. The molecular weight amounted to 1886.1.

Example 2

Synthesis of a Compound Comprising Amino Acid Sequence SEQ ID NO: 2

The compound comprising the amino acid sequence SEQ ID NO: 2 was synthesized fully automatically via Fmoc solid-phase synthesis in steps which are described in table 1 of example 1.

The ring closure was effected by the formation of an amide bond between the nitrogen of the delta-amino group of the side chain of the N-terminal ornithine and the carbon of the carboxyl group of the C-terminal glycine.

Subsequently, the peptide was examined via reverse HPLC. The purity was more than 95%. The molecular weight amounted to 1872.4.

Example 3

Synthesis of a Compound Comprising Amino Acid Sequence SEQ ID NO: 3

The compound comprising the amino acid sequence SEQ ID NO: 3 was synthesized fully automatically via Fmoc solid-phase synthesis in steps which are described in table 1 of example 1.

The ring closure was effected by the formation of an amide bond between the nitrogen of the amino group of the N-terminal glycine and the carbon C1 of the carboxyl group of the amino-pentanoic acid, on the one hand, and by the formation of an amide bond between the nitrogen of the amino group of the amino-pentanoic acid and the carbon of the carboxyl group of the C-terminal glycine, on the other hand.

Subsequently, the peptide was examined via reverse HPLC. The purity was more than 95%. The molecular weight amounted to 1857.0.

Example 4

Synthesis of a Compound Comprising Amino Acid Sequence SEQ ID NO: 4

The compound comprising the amino acid sequence SEQ ID NO: 4 was synthesized fully automatically via Fmoc solid-phase synthesis in steps which are described in table 1 of example 1.

The ring closure was effected by the formation of an amide bond between the nitrogen of the amino group of the N-terminal glycine and the carbon C1 of the carboxyl group of the gamma-aminobutyric acid, on the one hand, and by the formation of an amide bond between the nitrogen of the amino group of the gamma-aminobutyric acid and the carbon of the carboxyl group of the C-terminal glycine, on the other hand.

Subsequently, the peptide was examined via reverse HPLC. The purity was more than 95%. The molecular weight amounted to 1843.0.

Example 5

Synthesis of a Compound Comprising Amino Acid Sequence SEQ ID NO: 5

The compound comprising the amino acid sequence SEQ ID NO: 5 was synthesized fully automatically via Fmoc solid-phase synthesis in steps which are described in table 1 of example 1.

The ring closure was effected by the formation of an amide bond between the nitrogen of the amino group of the N-terminal glycine and the carbon C1 of the carboxyl group of the gamma-aminobutyric acid, on the one hand, and by the formation of an amide bond between the nitrogen of the amino group of the gamma-aminobutyric acid and the carbon of the carboxyl group of the side chain of the C-terminal aspartic acid, on the other hand.

Subsequently, the peptide was examined via reverse HPLC. The purity was more than 95%. The molecular weight amounted to 1901.0.

Example 6

Synthesis of a Compound Comprising Amino Acid Sequence SEQ ID NO: 6

The compound comprising the amino acid sequence SEQ ID NO: 6 was synthesized fully automatically via Fmoc solid-phase synthesis in steps which are described in table 1 of example 1.

The ring closure was effected by the formation of an amide bond between the nitrogen of the amino group of the N-terminal glycine and the carbon C1 of the carboxyl group of the 3-amino-propanoic acid, on the one hand, and by the formation of an amide bond between the nitrogen of the amino group of the 3-amino-propanoic acid and the carbon of the carboxyl group of the side chain of the C-terminal glutamic acid, on the other hand.

Subsequently, the peptide was examined via reverse HPLC. The purity was more than 95%. The molecular weight amounted to 1901.0.

Example 7

Synthesis of a Compound Comprising Amino Acid Sequence SEQ ID NO: 7

The compound comprising the amino acid sequence SEQ ID NO: 7 was synthesized fully automatically via Fmoc solid-phase synthesis in steps which are described in table 1 of example 1.

The ring closure was effected by the formation of an amide bond between the nitrogen of the amino group of the N-terminal glycine and the carbon C1 of the carboxyl group of the 7-amino-heptanoic acid, on the one hand, and by the formation of an amide bond between the nitrogen of the amino group of the 7-amino-heptanoic acid and the carbon of the carboxyl group of the C-terminal tyrosine, on the other hand.

Subsequently, the peptide was examined via reverse HPLC. The purity was more than 95%. The molecular weight amounted to 1828.0.

Example 8

Synthesis of a Compound Comprising Amino Acid Sequence SEQ ID NO: 8

The compound comprising the amino acid sequence SEQ ID NO: 8 was synthesized fully automatically via Fmoc solid-phase synthesis in steps which are described in table 1 of example 1.

The ring closure was effected by the formation of an amide bond between the nitrogen of the amino group of the N-terminal glycine and the carbon C1 of the carboxyl group of the 6-amino-hexanoic acid, on the one hand, and by the formation of an amide bond between the nitrogen of the amino group of the 6-amino-hexanoic acid and the carbon of the carboxyl group of the C-terminal glycine, on the other hand.

Subsequently, the peptide was examined via reverse HPLC. The purity was more than 95%. The molecular weight amounted to 1873.0.

Example 9

Patch-Clamp Experiments

9a. Cell Culture

The electrophysiological experiments were performed on human A549 cells (ATTC No. CCL-185). A549 cells are human lung epithelial cells which are involved in the diffusion of water and electrolytes in the lungs. The cells were suspended in RPMI-1640 medium (Sigma-Aldrich, product number R6504) with 1% penicillin/streptomycin and 10% fetal calf serum, transferred into plastic cell culture vessels and cultivated in an incubator with 95% air and 5% $CO_2$ at 37° C. The medium was changed 2 to 3 times per week. The cells double within approx. 22 hours, and a cell concentration of more than $7 \times 10^4$ cells per $cm^2$ was not exceeded.

9b. Addition of Compounds

The cells were microscopically observed. In doing so, it was found that also the respective addition of a compound comprising the amino acid sequence SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 did not produce any changes in morphology or cell growth, and the respective addition did not result in the death of cells.

9c. Patch-Clamp Experiments

For the patch-clamp experiments, the cells were transferred onto small glass plates.

9d. Patch-Clamp Measurements

Macroscopic currents were discharged from A549 cells in the "whole cell" configuration of the "patch-clamp" technique (Hamill et al, Pflugers Arch. 1981, 391(2):85-100, 1981). For the current dissipations in the "whole cell" configuration, the following bath and electrode solutions were used:

Bath solution: 135 mM sodium methanesulfonate, 10 mM NaCl, 2.7 mM KCl, 1.8 mM $CaCl_2$, 2 mM $MgCl_2$, 5.5 mM glucose, and 10 mM HEPES, pH 7.4.

Electrode solution: 120 mM potassium methanesulfonate, 15 mM KCl, 6 mM NaCl, 1 mM Mg2ATP, 2 mM Na3ATP, 10 mM HEPES, and 0.5 mM EGTA (pH 7.2).

Cover slips with the cells cultivated thereon were transferred into a test bath with a capacity of 1 ml, fixed on the microscope table (Axiovert 100, 400-fold magnification), and the cells were superfused with the above-described bath solution. Thereupon, the current was discharged from a suitable cell (which adheres to the cover slip). For this purpose, a microelectrode filled with an electrolyte solution (glass capillary with a defined, heat-polished tip opening of about 1-3 µm, corresponding to a resistance of the electrode tip of 3-5Ω) was placed on the cell and the membrane was sucked in so that a "Gigaohm seal" was formed between the membrane and the electrode in order to minimize the leakage current. In the "whole cell" configuration, the membrane was penetrated beneath the electrode tip so that the current flowing through all ion channels of the cell could be measured. Upon obtaining a Gigaohm seal, a defined membrane retaining potential was applied via a pre-amplifier (CV-4 Headstage, Axon Instruments) and an amplifier (Axopatch 1 D, Axon Instr.) and the current thereby flowing through the ion channels was measured.

The pulse protocol consisted of a hyperpolarization of the cell membrane to −100 mV for 5 s and a subsequent gradual depolarization to +100 mV in 20 mV steps.

This protocol was performed before (control) and after the addition of ring-shaped organic molecules. The current dissipations thus obtained were stored and analyzed by means of the program PCLAMP 6.0. For this purpose, the current dissipations obtained in the presence of amiloride were subtracted from the currents recorded earlier so that the amiloride-sensitive sodium current through the epithelial sodium channels could be determined.

9d. Results

Regulation of Sodium Ion Channels Via Compounds According to the Present Invention Using a patch-clamp measurement, the compounds according to the present invention were tested for their ability to regulate vectorial ion channels. In doing so, it became apparent that compounds according to the present invention have the ability to regulate vectorial ion channels.

In addition, compounds according to the present invention were compared to peptides known from the literature and their activity compared to that of known peptides was determined.

The results are summarized in table 2:

TABLE 2

| Identification | Structure | Activity in comparison to a peptide SEQ ID NO: 10 CGQRETPEGAEKPWYC ("TIP-Peptid", Lucas et al. Science 1994 also WO00/09149) |
| --- | --- | --- |
| SEQ ID NO: 2 from EP 2009 023 | SEQ ID NO: 11 CGTKPIELGPDEPKAVC | 80% |
| SEQ ID NO: 2 from PCT AT2008 448 | SEQ ID NO: 12 LSPGQRETPEGAEAKPWYE | 60% |
| SEQ ID NO: 1 according to the present invention | [KGQRETPEGAEAKPWYG] (cyclo Kepsilon1-G17) | 150% |
| SEQ ID NO: 2 according to the present invention | [ornithine-GQRETPEGAEAKPWYG] (cyclo Orn-delta1-G17) | 115% |
| SEQ ID NO: 5 according to the present invention | [gamma-aminobutyric acid-GQRETPEGAEAKPWYD-OH] (cyclo 1-Dγ17) | 160% |
| SEQ ID NO: 6 according to the present invention | [3-amino-propanoic acid-GQRETPEGAEAKPWYE-OH] | 150% |
| SEQ ID NO: 8 according to the present invention | [6-amino-hexanoic acid-GQRETPEGAEAKPWYG] (cyclo 1-17) | 150% |

As can be seen in table 2, the activity of compounds according to the present invention is surprisingly higher than the activity of structurally different known peptide compounds.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

SEQUENCE LISTING

```
<160> NUMBER OF SEQ ID NOS: 12

<210> SEQ ID NO 1
<211> LENGTH: 17
<212> TYPE: PRT
<213> ORGANISM: Artificial Sequence
<220> FEATURE:
<223> OTHER INFORMATION: cyclo Kepsilon1-G17
<220> FEATURE:
<221> NAME/KEY: TURN
<222> LOCATION: (1)..(17)
<223> OTHER INFORMATION: Ring closure between the N-terminal amino acid
      lysine (K) and the C-terminal amino acid glycine (G) via an amide
      bond between the nitrogen of the epsilon-amino group of the side
      chain of the lysine and the carbon of the carboxyl group of the
      glycine

<400> SEQUENCE: 1

Lys Gly Gln Arg Glu Thr Pro Glu Gly Ala Glu Ala Lys Pro Trp Tyr
1               5                   10                  15

Gly

<210> SEQ ID NO 2
<211> LENGTH: 17
<212> TYPE: PRT
<213> ORGANISM: Artificial Sequence
<220> FEATURE:
<223> OTHER INFORMATION: cyclo Orn-delta1-G17
<220> FEATURE:
<221> NAME/KEY: TURN
<222> LOCATION: (1)..(17)
<223> OTHER INFORMATION: Ring closure between the N-terminal Orn and
      the C-terminal Gly via an amide bond between the delta-amino
      group of the side chain of the ornithine and the carboxyl group
      of the glycine
```

```
<220> FEATURE:
<221> NAME/KEY: MOD_RES
<222> LOCATION: (1)..(1)
<223> OTHER INFORMATION: Orn

<400> SEQUENCE: 2

Xaa Gly Gln Arg Glu Thr Pro Glu Gly Ala Glu Ala Lys Pro Trp Tyr
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: cyclo 1-17
<220> FEATURE:
<221> NAME/KEY: TURN
<222> LOCATION: (1)..(16)
<223> OTHER INFORMATION: Ring closure between the N-terminal Gly and the
      C-terminal Gly via amide bonds between the N-terminal Gly amino
      group and the 5-amino-pentanoic acid C1-COOH and between the 5-
      amino-pentanoic acid 5-amino group and the C-terminal Gly

<400> SEQUENCE: 3

Gly Gln Arg Glu Thr Pro Glu Gly Ala Glu Ala Lys Pro Trp Tyr Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: cyclo 1-17
<220> FEATURE:
<221> NAME/KEY: TURN
<222> LOCATION: (1)..(16)
<223> OTHER INFORMATION: Ring closure between the C-terminal Gly and the
      N-terminal Gly via amide bonds between the N-terminal Gly amino
      group and the gamma-aminobutyric acid C1-COOH and between the
      gamma-aminobutyric acid amino group and the C-terminal Gly

<400> SEQUENCE: 4

Gly Gln Arg Glu Thr Pro Glu Gly Ala Glu Ala Lys Pro Trp Tyr Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: cyclo 1-Dgamma17
<220> FEATURE:
<221> NAME/KEY: TURN
<222> LOCATION: (1)..(16)
<223> OTHER INFORMATION: Ring closure between the C-terminal Asp and the
      N-terminal Gly via amide bonds between the N-terminal Gly NH2 and
      gamma-aminobutyric acid C1-COOH and between gamma-aminobutyric
      acid NH2 and the C-terminal Asp side chain COOH

<400> SEQUENCE: 5

Gly Gln Arg Glu Thr Pro Glu Gly Ala Glu Ala Lys Pro Trp Tyr Asp
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: cyclo 1-Edelta17
```

```
<220> FEATURE:
<221> NAME/KEY: TURN
<222> LOCATION: (1)..(16)
<223> OTHER INFORMATION: Ring closure between the C-terminal Glu and the
      N-terminal Gly via amide bonds between the N-terminal Gly NH2 and
      the 3-amino-propanoic acid  C1-COOH and between the 3-amino-
      propanoic acid NH2 and the C-terminal Glu side chain COOH

<400> SEQUENCE: 6

Gly Gln Arg Glu Thr Pro Glu Gly Ala Glu Ala Lys Pro Trp Tyr Glu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: cyclo 1-16
<220> FEATURE:
<221> NAME/KEY: TURN
<222> LOCATION: (1)..(15)
<223> OTHER INFORMATION: Ring closure between the C-terminal Tyr and the
      N-terminal Gly via amide bonds between the N-terminal Gly amino
      group and the 7-amino-heptanoic acid C1-carboxyl group and between
      the 7-amino-heptanoic acid amino group and the Tyr car

<400> SEQUENCE: 7

Gly Gln Arg Glu Thr Pro Glu Gly Ala Glu Ala Lys Pro Trp Tyr
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: cyclo 1-17
<220> FEATURE:
<221> NAME/KEY: TURN
<222> LOCATION: (1)..(16)
<223> OTHER INFORMATION: Ring closure between the C-terminal Gly and the
      N-terminal Gly via amide bonds between the N-terminal Gly amino
      group and the 6-amino-hexanoic acid C1-COOH and between the 6-
      amino-hexanoic acid amino group and the C-terminal Gly COOH

<400> SEQUENCE: 8

Gly Gln Arg Glu Thr Pro Glu Gly Ala Glu Ala Lys Pro Trp Tyr Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Basic structural element of the cyclic organic
      compounds according to the invention

<400> SEQUENCE: 9

Gly Gln Arg Glu Thr Pro Glu Gly Ala Glu Ala Lys Pro Trp Tyr
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: peptide published in WO 00/09149

<400> SEQUENCE: 10

Cys Gly Gln Arg Glu Thr Pro Glu Gly Ala Glu Lys Pro Trp Tyr Cys
1               5                   10                  15
```

```
<210> SEQ ID NO 11
<211> LENGTH: 17
<212> TYPE: PRT
<213> ORGANISM: Artificial Sequence
<220> FEATURE:
<223> OTHER INFORMATION: peptide published in EP 2 009 023

<400> SEQUENCE: 11

Cys Gly Thr Lys Pro Ile Glu Leu Gly Pro Asp Glu Pro Lys Ala Val
1               5                   10                  15

Cys

<210> SEQ ID NO 12
<211> LENGTH: 19
<212> TYPE: PRT
<213> ORGANISM: Artificial Sequence
<220> FEATURE:
<223> OTHER INFORMATION: peptide published in WO 2009/073909

<400> SEQUENCE: 12

Leu Ser Pro Gly Gln Arg Glu Thr Pro Glu Gly Ala Glu Ala Lys Pro
1               5                   10                  15

Trp Tyr Glu
```

We claim:

1. A cyclic organic compound, consisting of an amino acid sequence wherein the amino acid sequence is SEQ ID NO:9 GQRETPEGAEAKPWY in addition to one or two further amino acids, wherein said sequence has no carboxyl group C-terminally and/or no amino group N-terminally, wherein a ring closure is formed between a side chain of one amino acid and the C-terminus of another amino acid, or the ring closure is effected with the aid of a nonnatural amino acid, and wherein one of the additional amino acids is a nonnatural amino acid, selected from the group consisting of ornithine and an omega-amino acid, or the cyclic organic compound is a compound wherein the compound is SEQ ID NO: 1

HN-Gly-Gln-Arg-Glu-Thr-Pro-Glu-Gly-Ala-Glu-Ala-Lys-Pro-Trp-Tyr-Gly—
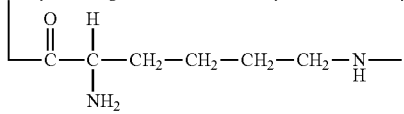

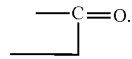

2. The compound according to claim 1, wherein the ring closure is formed between a side chain of the nonnatural amino acid ornithine or lysine and the C-terminus of a natural amino acid.

3. The compound according to claim 1, wherein the ring closure is formed between a side chain of ornithine or lysine and the C-terminus of glycine.

4. The compound according to claim 1, wherein the compound is a compound of the formula selected from the group consisting of

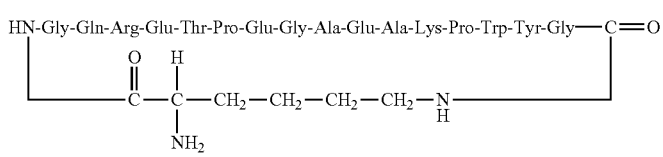

SEQ ID NO: 1

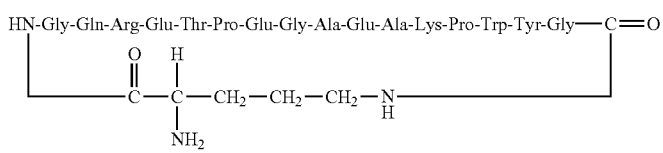

SEQ ID NO: 2

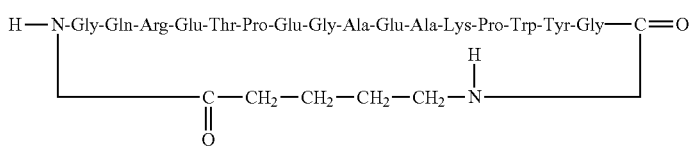

SEQ ID NO: 3

-continued

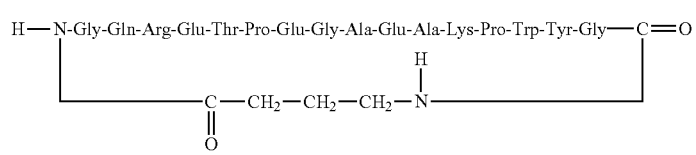
SEQ ID NO: 4

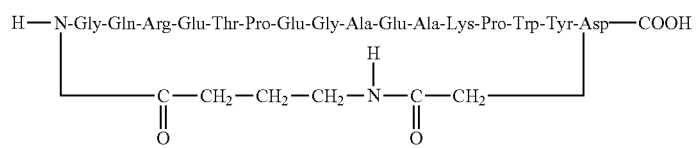
SEQ ID NO: 5

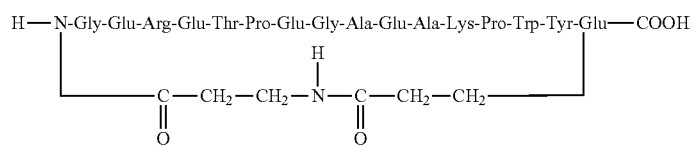
SEQ ID NO: 6

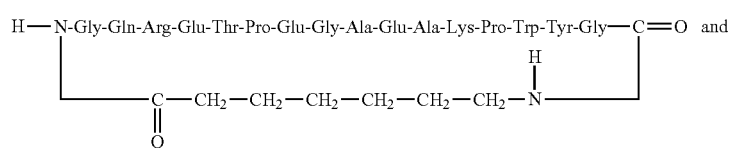
SEQ ID NO: 7 and

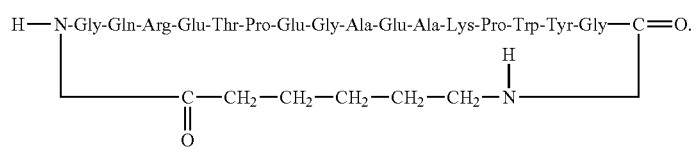
SEQ ID NO: 8

5. A compound according to claim 1, wherein said compound is in the form of a salt.

6. The compound according to claim 1, wherein said compound is used as a medicament for regulating vectorial ion channels, treating diseases associated with the lung function and treating oedemas.

7. A pharmaceutical preparation, comprising a compound according to claim 1 in combination with at least one pharmaceutically acceptable adjuvant.

8. The pharmaceutical preparation according to claim 7, wherein said at least one pharmaceutically acceptable adjuvant is selected from the group consisting of carriers and diluents.

9. The pharmaceutical preparation according to claim 8, wherein said group consisting of carriers and diluents is at least one selected from the group consisting of fillers, binders, disintegrants, flow-conditioning agents, lubricants, flavouring agents, sugar or sweeteners, fragrances, preservatives, substances having a stabilizing effect, wetting agents, emulsifiers, solubilizers, salts for regulating the osmotic pressure and buffer (mixtures).

* * * * *